(12) United States Patent
Carter

(10) Patent No.: US 8,491,882 B2
(45) Date of Patent: Jul. 23, 2013

(54) METHODS FOR REDUCING THE RISK OF AN UNSUCCESSFUL PREGNANCY IN A SUBJECT HAVING AN IMMUNE SYSTEM ABBERATION

(75) Inventor: Darryl L. Carter, Owings Mills, MD (US)

(73) Assignee: Nora Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 13/342,512

(22) Filed: Jan. 3, 2012

(65) Prior Publication Data

US 2012/0315243 A1 Dec. 13, 2012

Related U.S. Application Data

(63) Continuation of application No. 12/951,704, filed on Nov. 22, 2010, now abandoned, which is a continuation of application No. 12/433,999, filed on May 1, 2009, now abandoned, which is a continuation-in-part of application No. 12/238,977, filed on Sep. 26, 2008, now abandoned, which is a continuation of application No. 11/411,361, filed on Apr. 24, 2006, now Pat. No. 7,470,662, which is a continuation of application No. PCT/US2004/035468, filed on Oct. 25, 2004.

(60) Provisional application No. 60/514,472, filed on Oct. 24, 2003.

(51) Int. Cl.
*A61K 45/00* (2006.01)
*A61K 38/00* (2006.01)

(52) U.S. Cl.
USPC ............ 424/85.1; 514/1.1; 530/350; 530/351

(58) Field of Classification Search
None
See application file for complete search history.

(56) References Cited

U.S. PATENT DOCUMENTS

| | | | |
|---|---|---|---|
| 4,554,101 A | 11/1985 | Hopp et al. | |
| 5,104,651 A | 4/1992 | Boone et al. | |
| 5,147,799 A | 9/1992 | Bursuker et al. | |
| 5,276,017 A | 1/1994 | Feinberg et al. | |
| 5,284,656 A | 2/1994 | Platz et al. | |
| 5,320,840 A | 6/1994 | Camble et al. | |
| 5,399,345 A | 3/1995 | Schumacher et al. | |
| 5,416,195 A | 5/1995 | Camble et al. | |
| 5,422,248 A | 6/1995 | Smith et al. | |
| 5,766,944 A | 6/1998 | Ruiz | |
| 5,837,230 A | 11/1998 | Nakai et al. | |
| 5,888,495 A | 3/1999 | Schrier et al. | |
| 5,891,429 A | 4/1999 | Clark et al. | |
| 5,895,646 A | 4/1999 | Wang | |
| 5,908,763 A | 6/1999 | Clark et al. | |
| 5,919,757 A | 7/1999 | Michaelis et al. | |
| 5,981,551 A | 11/1999 | Luengo et al. | |
| 5,989,537 A | 11/1999 | Holly et al. | |
| 6,040,340 A * | 3/2000 | Chwalisz et al. | ............. 514/509 |
| 6,150,085 A | 11/2000 | Hess et al. | |
| 6,162,417 A | 12/2000 | Goodman et al. | |
| 6,162,427 A | 12/2000 | Baumann et al. | |
| 6,166,183 A | 12/2000 | Ishikawa et al. | |
| 6,261,550 B1 | 7/2001 | Osslund | |
| 6,277,379 B1 | 8/2001 | Oaks et al. | |
| 6,565,841 B1 | 5/2003 | Niven et al. | |
| 6,646,110 B2 | 11/2003 | Nissen et al. | |
| 6,946,548 B2 | 9/2005 | Sarkar et al. | |
| 6,979,674 B1 | 12/2005 | Goldenberg et al. | |
| 7,470,662 B2 | 12/2008 | Carter | |
| 7,615,531 B2 | 11/2009 | Carter | |
| 7,700,548 B2 | 4/2010 | Carter | |
| 7,744,864 B2 | 6/2010 | Carter | |
| 7,824,712 B2 | 11/2010 | Carter | |
| 7,939,491 B2 | 5/2011 | Carter | |
| 8,338,373 B2 | 12/2012 | Carter | |
| 2001/0009922 A1 | 7/2001 | Faller et al. | |
| 2003/0068664 A1 | 4/2003 | Albitar et al. | |
| 2003/0166527 A1 | 9/2003 | Sarkar et al. | |
| 2004/0105858 A1 | 6/2004 | Kim et al. | |
| 2004/0137557 A1 | 7/2004 | DeFrees et al. | |
| 2004/0224393 A1 | 11/2004 | Kwon et al. | |
| 2009/0226397 A1 | 9/2009 | Carter | |
| 2012/0263673 A1 | 10/2012 | Carter | |
| 2012/0269763 A1 | 10/2012 | Carter | |

FOREIGN PATENT DOCUMENTS

| | | |
|---|---|---|
| WO | 2005/039505 | 5/2005 |
| WO | 2006/128176 | 11/2006 |
| WO | 2008/009705 | 1/2008 |

OTHER PUBLICATIONS

Arpaci et al., "A Successful and Simplified Filgrastim Primed Single Apheresis Method Without Large Volume Apheresis for Peripheral Blood Stem Cell Collection," *Jpn. J. Clin. Oncol.* 30(3): 153-158, 2000.

Berenson et al., "Transplantation of CD34+ Hematopoietic Progenitor Cells," *Cancer Investigation* 14(6): 589-596, 1996.

Bueno et al., "Endoscopic placement of direct percutaneous jejunostomy tubes in patients with complications after esophagectomy," *Gastrointestinal Endoscopy* 57(4): 536-540, 2003.

Calhoun et al., "A randomized pilot trial of administration of granulocyte colony-stimulating factor to women before preterm delivery," *American Journal of Obstetrics & Gynecology* 179: 766-771, 1998.

Cameo et al., "Similar embryotoxic effects of sera from infertile patients and exogenous interferon-γ on long-term in-vitro development of mouse embryos," *Human Reproduction* 14(4): 959-963, 1999.

(Continued)

*Primary Examiner* — Gyan Chandra
(74) *Attorney, Agent, or Firm* — Seed IP Law Group PLLC

(57) ABSTRACT

Methods and kits for preventing or reducing the likelihood of implantation failure or miscarriage in a recipient of artificial insemination are provided. The methods include administering into a recipient of artificial insemination in need of such treatment an effective amount of granulocyte colony stimulating factor (G-CSF).

45 Claims, No Drawings

OTHER PUBLICATIONS

Cavallaro et al., "Three to six year follow-up of normal donors who received recombinant human granulocyte colony-stimulating factor," *Bone Marrow Trans.* 25: 85-89, 2000.

Chaouat et al., "Implantation: can immunological parameters of implantation failure be of interest for preeclampsia?," *Journal of Reproductive Immunology* 59: 205-217, 2003.

Clark et al., "Prevention of spontaneous abortion in DBA/2-mated CBA/J mice by GM-CSF involves CD8+ T cell-independent suppression of natural effector cell cytotoxicity against trophoblast target cells," *Cellular Immunology* 154: 143-152, 1994.

Clark et al., "Unexplained sporadic and recurrent miscarriage in the new millennium: a critical analysis of immune mechanisms and treatments," *Human Reproduction Update* 7:501-511, 2001.

Delagrave et al., "Recursive ensemble mutagenesis," *Protein Engineering* 6(3): 327-331, 1993.

Deng et al., "Site-Directed Mutagenesis of Virtually Any Plasmid by Eliminating a Unique Site," *Analytical Biochemistry* 200: 81-88, 1992.

Doncarli et al., "Conversion in vivo from an early dominant Th0/Th1 response to a Th2 phenotype during the development of collagen-induced arthritis," *Eur. J. Immunol.* 27: 1451-1458, 1997.

Dreger et al., "G-CSF-mobilized peripheral blood progenitor cells for allogenic transplantation: safety, kinetics of mobilization, and composition of the graft," *British Journal of Haematology* 87: 609-613, 1994.

Duan et al., "Production of granulocyte colony stimulating factor in decidual tissue and its significance in pregnancy," *Osaka City Med. J.* 36: 81-97, 1990.

Dudrick et al., "Total Parenteral Nutrition: Techniques, Complications, and Prevention," *Surgical Technology International VII*: 174-184, 1998.

Fukunaga et al., "Purification and Characterization of the Receptor for Murine Granulocyte Colony-stimulating Factor," *The Journal of Biological Chemistry* 266(23): 14008-14015, Aug. 15, 1990.

Griebel et al., "Management of Spontaneous Abortion," *American Family Physician* 72(7): 1243-1250, Oct. 1, 2005.

Huang et al., "Maintaining hyporesponsiveness and polarization potential of T cells after in vitro mixture of G-CSF mobilized peripheral blood grafts and G-CSF primed bone marrow grafts in different proportions," *Transplant Immunology* 17: 193-197, 2007.

Kocherlakota et al., "Preliminary Report: rhG-CSF May Reduce the Incidence of Neonatal Sepsis in Prolonged Preeclampsia-associated Neutropenia," *Pediatrics* 102: 1107-1111, 1998.

Kozak, "At Least Six Nucleotides Preceding the AUG Initiator Codon Enhance Translation in Mammalian Cells," *J. Mol. Biol.* 196: 947-950, 1987.

Krishnan et al., "T Helper 1 Response Against Leishmania major in Pregnant C57BL/6 Mice Increases Implantation Failure and Fetal Resorptions," *The Journal of Immunology* 156: 653-662, 1996.

Kwak-Kim et al., "Increased T helper 1 cytokine responses by circulating T cells are present in women with recurrent pregnancy losses and in infertile women with multiple implantation failures after IVF," *Human Reproduction* 18(4): 767-773, 2003.

Lecoeur et al., "Strategies for phenotyping apoptotic peripheral human lymphocytes comparing ISNT, annexin-V and 7-AAD cytofluorometric staining methods," *Journal of Immunological Methods* 209: 111-123, 1997.

Link et al., "CD34 Positive Blood Cells for Allogeneic Progenitor and Stem Cell Transplantation," *Leukemia and Lymphoma* 26: 451-465, 1997 [current as of Jul. 22, 2008].

Matsubara et al., "Concentrations of Serum Granulocyte-Colony-Stimulating Factor in Normal Pregnancy and Preeclampsia," *Hypertension in Pregnancy* 18: 95-106, 1999.

Mauri et al., "Relationship between Th1/Th2 cytokine patterns and the arthritogenic response in collagen-induced arthritis," *Eur. J. Immunol.* 26: 1511-1518, 1996.

Medlock et al., "Granulocyte colony-stimulating factor crosses the placenta and stimulates fetal rat granulopoiesis," *Blood* 81(4): 916-922, 1993.

Merck Manual 17$^{th}$ edition, Merck Research Laboratories, Whitehouse Station, New Jersey, Chapter 252, pp. 2053-2061, 1999.

Merck Manual 17$^{th}$ edition, Merck Research Laboratories, Whitehouse Station, New Jersey, p. 1995 (1999).

Mohandas et al., "Total parenteral nutrition," *The National Medical Journal of India* 16(1): 29-33, 2003.

Mori et al, "Immunomolecular mechanisms in mammalian Implantation," *Endocrine Journal* 41(Supp): s17-s31, 1994.

Morris et al., "Stem cell mobilization with G-CSF analogs: a rational approach to separate GVHD and GVL?," *Blood* 107(9): 3430-3435, May 1, 2006.

Moverare et al., "Study of the Th1/Th2 balance, including IL-10 production, in cultures of peripheral blood mononuclear cells from birch-pollen-allergic patients," *Allergy* 55: 171-175, 2000.

Okkels, "A URA3 promoter deletion in a pYES vector increases the expression level of preferred delivery method," *Ann. NY Acad. Sci.* 782: 202-207, 1996.

Oksenberg et al., "In Vitro Suppression of Murine Blastocysts Growth by Sera From Women With Reproductive Disorders," *American Journal of Reproductive Immunology and Microbiology* 11: 118-124, 1986.

Papadimitriou et al., "Non-Cryopreserved Peripheral Blood Progenitor Cells Collected by a Single Very Large-Volume Leukapheresis: A Simplified and Effective Procedure for Support of High-Dose Chemotherapy," *Journal of Clinical Apheresis* 15: 236-241, 2000.

Perricone et al., "GM-CSF and pregnancy: Evidence of significantly reduced blood concentrations in unexplained recurrent abortion efficiently reverted by intravenous immunoglobulin treatment," *American Journal of Reproductive Immunology* 50: 232-237, 2003.

Raghupathy et al., "Cytokine production by maternal lymphocytes during normal human pregnancy and in unexplained recurrent spontaneous abortion," *Human Reproduction* 15: 713-718, 2000.

Raghupathy et al., "Maternal Th1- and Th2-Type Reactivity to Placental Antigens in Normal Human Pregnancy and Unexplained Recurrent Spontaneous Abortions," *Cellular Immunology* 196: 122-130, 1999.

Raziuddin et al., "Divergent Cytokine Production Profile in Behçet's Disease. Altered Th1/Th2 Cell Cytokine Pattern," *The Journal of Rheumatology* 25(2): 329-333, 1998.

Reidhaar-Olson et al., "Random Mutagenesis of Protein Sequences Using Oligonucleotide Cassettes," *Methods in Enzymology* 208: 564-568, 1991.

Reidhaar-Olson et al., "Identification of Residues Critical to the Activity of Human Granulocyte Colony-Stimulating Factor," *Biochemistry* 35: 9034-9041, 1996.

Rezaei et al., "T-helper (1) cytokines increase during early pregnancy in women with a history of recurrent spontaneous abortion," *MedSciMonit* 8(8): CR607-610, 2002.

Roussev et al., "Validation of an Embryotoxicity Assay," *American Journal of Reproductive Immunology* 33: 171-175, 1995.

Saito et al., "Elevation of Amniotic Fluid Interleukin 6 (IL-6), IL-8 and Granulocyte Colony Stimulating Factor (G-CSF) in Term and Preterm Parturition," *CYTOKINE* 5(1): 81-88, Jan. 1993.

Sanger et al., "DNA sequencing with chain-terminating inhibitors," *Proc. Natl. Acad. Sci. USA* 74(12): 5463-5467, Dec. 1997.

Scarpellini et al., "Effectiveness of GM-CSF 1 in the treatment of habitual abortion in a controlled study," *Fertility and Sterility* 80(Suppl 3): S288, 2003.

Scarpellini et al., "Effectiveness of GM-CSF 1 in the Treatment of Habitual Abortion in a Controlled Study," *American Journal of Reproductive Immunology (Abstracts)* 51: 433-434, 2004.

Schust et al., "Correlation of Serum Cytokine and Adhesion Molecule Determinations With Pregnancy Outcome," *J. Soc. Gynecol. Invest.* 3(5): 259-261, Sep./Oct. 1996.

Shike et al., "Direct percutaneous endoscopic jejunostomies for enteral feeding," *Gastrointestinal Endoscopy* 44(5): 536-540, 1996.

Stemmer et al., "Single-step assembly of a gene and entire plasmid from large numbers of oligodeoxyribonucleotides," *Gene* 164: 49-53, 1995.

Stephenson et al., "Evaluation and Management of Recurrent Early Pregnancy Loss," *Clinical Obstetrics and Gynecology* 50(1): 132-145, Mar. 2007.

Sullivan et al., "Recurrent Fetal Aneuploidy and Recurrent Miscarriage," *Obstetrics & Gynecology* 104(4): 784-788, Oct. 2004.

Sun et al., "IFN-γ Promotes Apoptosis of the Uterus and Placenta in Pregnant Rat and Human Cytotrophoblast Cells," *Journal of Interferon & Cytokine Research* 27: 567-578, 2007.

Thomason et al., "Prevalence of Embryotoxic Factor in Sera From Women With Unexplained Recurrent Abortion," *American Journal of Reproductive Immunology* 34: 338-341, 1995.

Vogel et al., "Clinical Applications of CD34+ Peripheral Blood Progenitor Cells (PBPC)," *Stem Cells* 18: 87-92 2000.

Wells et al., "Casette mutagenesis: an efficient method for generation of multiple mutations at defined sites," *Gene* 34(2-3): 315-323, 1985.

Xing et al., "Th1/Th2 type cytokines in hepatitis B patients treated with interferon-α," *Chinese Medical Journal* 114(9): 921-924, 2001.

Yabuki et al., "Giant Lysosomes in the Renal Proximal Tubules—A Morphological Characteristic of DBA/2 and DBA/1 Mouse Kidneys," *Exp. Anim.* 52(2): 159-163, 2003.

Younghusband et al., "Mutagenesis of conserved 5' elements and transcription of a chicken H1 histone gene," *Nucleic Acids Research* 14(2): 635-644, 1986.

Zell et al., "DNA mismatch-repair in *Escherichia coli* counteracting the hydrolytic deamination of 5-methyl-cytosine residues," *The EMBO Journal* 6(6): 1809-1815, 1987.

European Search Report (European Application No. 04796441.6 filed Oct. 25, 2004).

International Search Report (International Application No. PCT/U504/35468 filed Oct. 25, 2004).

International Search Report and Written Opinion of the International Searching Authority (International Application No. PCT/US2009/042481, filed May 1, 2009).

Kaufmann et al, "Term delivery in a woman with severe congenital neutropenia, treated with growth colony stimulating factor," *Human Reproduction* 13(2): 498-499; 1998.

Sbracia et al, "Use of GM-CSF 1 in the Treatment of Habitual Abortion: a Pilot Study," *Fertility & Sterility* 70(3): S62-S63; 1998.

Wurfel, "Approaches to a Better Implantation," *Journal of Assisted Reproduction and Genetics* 17(8): 473; 2000.

Boxer et al, "1490 Outcomes of Pregnancies for Women with Severe Chronic Neutropenia with or without G-CSF Treatment," 53$^{rd}$ *ASH Annual Meeting and Exposition*: Dec. 10-13, 2011.

Arpinati et al., "Granulocyte-colony stimulating factor mobilizes T helper 2-inducing dendritic cells," *Blood* 95: 2484-2490, 2000.

Chedraui et al., "Increased plasma soluble fms-like tyrosine kinase 1 and endoglin levels in pregnancies complicated with preeclampsia," *J. Matern. Fetal Neonatal Med.* 22(7): 565-570, Jul. 2009.

Conrad et al., "Placental Cytokines and the Pathogenesis of Preeclampsia," *American Journal of Reproductive Immunology* 37: 240-249, 1997.

Daher et al., "Tumor necrosis factor during pregnancy and at the onset of labor and spontaneous abortion," *European Journal of Obstetrics & Gynecology and Reproductive Biology* 83: 77-79, 1999.

Hill et al., "T-helper 1-Type Immunity to Trophoblast in Women With Recurrent Spontaneous Abortion," *Journal of the American Medical Association* 273(24): 1933-1936, Jun. 28, 1995.

Liu et al., "Introduction: TH2-inducing DC2 for immunotherapy," *Blood* 95: 2482-2483, 2000.

Ogasawara et al., "Elevation of Transforming Growth Factor-β1 Is Associated with Recurrent Miscarriage," *Journal of Clinical Immunology* 20(6): 453-457, 2000.

Pampfer et al., "Role of Colony Stimulating Factor-1 (CSF-1) and Other Lympho-hematopoietic Growth Factors in Mouse Pre-implantation Development." *BioEssays: News and Reviews in Molecular, Cellular and Developmental Biology* 13(10): 535-540, Oct. 1991.

Raghupathy, "Th1-type immunity is incompatible with successful pregnancy," *Immunology Today* 18(10): 478-482, Oct. 1997.

Saito et al., "Th1/Th2 balance in preeclampsia," *Journal of Reproductive Immunology* 59(2): 161-173, Aug. 2003.

Shurin et al., "Th1/Th2 balance in cancer, transplantation and pregnancy," *Springer Seminars in Immunopathology* 21: 339-359, 1999.

Sivakumaran, "Correspondence to the editor: Modulation of Th1/Th2 subsets by granulocyte-colony stimulating factor," *Blood* 97(1): 333, Jan. 1, 2001.

Sloand et al., "Pharmacologic doses of granulocyte colony-stimulating factor affect cytokine production by lymphocytes in vitro and in vivo," *Blood* 95: 2269-2274, 2000.

Sloand et al., "Response: Pharmacologic concentrations of granulocyte-colony stimulating factor affect cytokine expression by lymphocytes," *Blood* 97(1): 334-335, Jan. 1, 2001.

Vasconcelos et al., "Correspondence to the editor: Th1/Th2 lymphokine profile of T cells present in the blood of granulocyte-colony stimulating factor-treated stem-cell donors: up or down modulation?," *Blood* 97(1): 333-334, Jan. 1, 2001.

International Preliminary Report on Patentability mailed Nov. 6, 2007, for PCTAN PCT/US2004/035468, 5 pages.

European Search Report mailed Jun. 4, 2010, for EP 10159565, 7 pages.

Pan et al., "Pretreatment of Donor Mice With Granulocyte Colony-Stimulating Factor Polarizes Donor T Lymphocytes Toward Type-2 Cytokine Production and Reduces Severity of Experimental Graft-Versus-Host Disease," *Blood* 86(12): 4422-4429, Dec. 15, 1995.

\* cited by examiner

METHODS FOR REDUCING THE RISK OF AN UNSUCCESSFUL PREGNANCY IN A SUBJECT HAVING AN IMMUNE SYSTEM ABBERATION

CROSS-REFERENCE TO RELATED APPLICATIONS

This application is a continuation of U.S. patent application Ser. No. 12/951,603, filed Nov. 22, 2010, now abandoned; which is a continuation of U.S. patent application Ser. No. 12/433,999, filed on May 1, 2009, now abandoned; which is a continuation-in-part of U.S. patent application Ser. No. 12/238,977, filed Sep. 26, 2008, now abandoned; which is a continuation of U.S. patent application Ser. No. 11/411,361, filed Apr. 24, 2006 (U.S. Pat. No. 7,470,662); which is a continuation of PCT/US2004/035468, filed Oct. 25, 2004; which claims priority from U.S. Provisional Application No. 60/514,472, filed Oct. 24, 2003. All of these applications are incorporated herein by reference in their entireties.

FIELD

The present invention generally relates to methods of preventing implantation failure or miscarriage during assisted reproduction and, in particular, to methods for reducing the likelihood of or preventing implantation failure or miscarriage in recipients of intravaginal insemination, intracervical insemination, intratubal insemination, and intrauterine insemination.

BACKGROUND

Accompanying the rising age of hopeful parents is the increasing use of assisted reproductive techniques such as artificial insemination, in vitro fertilization (IVF), gamete intrafallopian tube transfer (GIFT), and the like. Artificial insemination (AI) is the process by which sperm is placed into the reproductive tract of a female for the purpose of impregnating the female by using means other than sexual intercourse. In humans, it is used as assisted reproductive technology, primarily to treat infertility but is also increasingly used to enable women without a male partner to produce children by using sperm provided by a sperm donor. Specifically, in artificial insemination, freshly ejaculated sperm, or sperm which has been frozen and thawed, is placed in the cervix (intracervical insemination or ICI), in the female's uterus (intrauterine insemination or IUD, in the vagina (intravaginal insemination or IVI), or in the fallopian tubes (intratubal insemination or ITI) by artificial means.

The American Society for Reproductive Medicine estimates that the success rate of artificial insemination may be as high as 15 percent each cycle. Although success rates are higher for other forms of fertility treatments, artificial insemination is often one of the first methods used. It is less invasive and less expensive than more complex procedures, such as in vitro fertilization.

Conception, pregnancy and delivery require an intricate and delicate interplay of physiology and anatomy. Implantation and placentation are complex processes involving hormonal, immune, and anatomical changes in the mother and migration and cellular division of the embryo.

Although pregnancy rates following six cycles of AI or one cycle of IVF can be as high as 60%, some recipients fail repeatedly. Various uterine pathologies, such as thin endometrium, altered expression of adhesive molecules and immunological factors, may be the causes for repeated failure.

Spontaneous abortion occurs in 15%-50% of diagnosed pregnancies in women between fifteen and forty-five years of age. The formal definition of recurrent spontaneous abortion is three or more spontaneous abortions. However, the American College of Obstetrics and Gynecology recommends that in women over the age of 35, a thorough workup should be undertaken after two spontaneous abortions. Approximately 3-4% of women are estimated to fit the formal definition of recurrent spontaneous abortion. The risk of pregnancy loss increases from 15-20% in the first pregnancy to 40% after one spontaneous abortion.

Although many pregnancies lost in the first trimester are due to fetal causes; spontaneous abortion, the loss of the products of conception prior to the 20th week of pregnancy, is often a disorder of unknown etiology. It has been theorized that spontaneous abortions are a natural rejection of a fetus with abnormalities incompatible with life; however, this theory has yet to be substantiated.

Risk factors for miscarriage include age, weight and overall health of the woman. The prevalence of spontaneous abortion increases with increasing maternal age, although not with gravidity. The risk begins to increase rapidly at age 35 years. The risk of spontaneous abortion at age 40 is approximately twice that at age 20. As families are planned later and later in life, the frequency of spontaneous abortion will only increase without effective methods of prevention.

Threatened abortion generally presents as cramping and bleeding for which treatment is bed rest. This conservative treatment provides palliative care for the mother but does little to alter the outcome. The use of hormones is generally contraindicated due to the risk of congenital anomalies, including malformation of the vessels of the heart of the embryo and possible genital abnormalities in female offspring.

Preeclampsia and other hypertensive disorders of pregnancy are a leading global cause of maternal and infant illness and death. Symptoms of preeclampsia include hypertension, edema and proteinuria with sudden weight gain, headaches and changes in vision. Preeclampsia can prevent the placenta from getting enough blood which can cause low birth weight and other problems for the baby. Although most women with preeclampsia still deliver healthy babies, some develop eclampsia, a serious condition that threatens the life of the mother and the fetus.

The risk of preeclampsia is higher in women carrying multiple babies, in teenage mothers and in women older than age 40. Typically, preeclampsia occurs in the late 2nd or 3rd trimesters (middle to late pregnancy) though occasionally it occurs earlier. Preeclampsia affects about 5% of all pregnancies.

Mild preeclampsia is conservatively treated with strict bed rest and vigilant monitoring of blood pressure. Progression of the disorder is treated with fluids, antihypertensives and magnesium sulfate but delivery of the fetus provides the only remedy.

In addition to the physical toll of these disorders, the loss of a desired pregnancy takes a tremendous emotional toll on hopeful and expectant parents. Loss of a pregnancy can lead to feelings of inadequacy, hopelessness and guilt which can have a devastating effect on individuals and on a marriage.

New methods and compositions are always needed to reduce risks associated with pregnancy to the health of the mother and fetus. Effective prevention of implantation failure or spontaneous abortion can allow women, especially women at risk, to have successful pregnancies. In particular, effective prevention of these disorders in women who suffer from infertility can allow women, especially women who seek medical care in the form of assisted reproduction like artificial insemination to have successful pregnancies. Prevention of implantation failure during assisted reproduction allows successful pregnancies, reduces the risks to women, and saves time and money.

SUMMARY

One objective of the present invention is to provide methods, compositions and kits comprising a granulocyte colony stimulating factor (G-CSF) in an amount effective to prevent miscarriage or implantation failure in an artificial insemination procedure.

One aspect of the present invention relates to a method for preventing or reducing the likelihood of implantation failure or miscarriage in a recipient of artificial insemination. The method comprises administering to the recipient of artificial insemination an effective amount of a composition comprising G-CSF.

In one embodiment, the artificial insemination is intrauterine insemination, intravaginal insemination, intracervical insemination, or intratubal insemination.

In another embodiment, the composition is administered parenterally, administered enterally, or topically.

In another embodiment, the composition is administered by inhalation.

In another embodiment, the composition is administered prior to the artificial insemination.

In another embodiment, the insemination is preceded by a controlled ovarian hyperstimulation procedure, and the composition is administered before, during, or after the time of controlled ovarian hyperstimulation.

In another embodiment, the composition is administered daily for one to thirty-five consecutive days.

In another embodiment, the composition is administered daily until the end of the first trimester.

In another embodiment, the composition is administered daily until the recipient presents a normal Th1 response or a normal Th2 response or both.

In another embodiment, the G-CSF is administered at a dose of between 0.1 mcg/kg/day to 600 mcg/kg/day.

In another embodiment, the G-CSF is administered at a dose of between 0.5 mcg/kg/day to 300 mcg/kg/day.

In another embodiment, the G-CSF is administered at a dose of between 1 mcg/kg/day to 100 mcg/kg/day.

In another embodiment, the G-CSF is administered at a dose of between 1 mcg/kg/day to 50 mcg/kg/day.

In another embodiment, the G-CSF is administered at a dose of between 1 mcg/kg/day to 10 mcg/kg/day.

In another embodiment, the G-CSF is administered at a dose of between 1 mcg/kg/day to 2 mcg/kg/day.

In another embodiment, the G-CSF is administered in the form of a nucleotide sequence encoding G-CSF.

In another embodiment, the composition further comprises an additive selected from the group consisting of cytokines that suppress Th1 immune response, cytokines that enhance Th2 immune response, cytokines that support successful pregnancy through non-immunologic mechanisms, anti-inflammatory agents, and inhibitors of pro-inflammatory cytokines.

In another embodiment, the additive is selected from the group consisting of interferon alpha, interferon beta, macrophage colony stimulating factor (M-CSF), granulocyte macrophage colony stimulating factor (GM-CSF), leukemia inhibitory factor (LIF), transforming growth factor beta (TGF-beta), interleukin-1(IL-1), IL-3, IL-4, IL-6, IL-7, IL-8, IL-9, IL-10, IL-11, IL-13, IL-14, IL-15, IL-19, IL-20, IL-21, IL-22, IL-24, IL-25, IL-26, IL-27, IL-28, IL-29, IL-30, IL-31, IL-32, IL-33, and IL-35.

In another embodiment, the composition further comprises a pharmaceutically acceptable carrier.

Another aspect of the present invention relates to a kit for preventing or reducing the likelihood of implantation failure and miscarriage in a recipient of artificial insemination. The kit includes an effective amount of G-CSF; and a label with instructions for using the G-CSF to prevent or reduce the likelihood of implantation failure and miscarriage.

Another aspect of the present invention relates to methods of preventing spontaneous abortion by administering an effective amount of G-CSF to the subject. The methods can be administered to any female subject at risk for spontaneous abortion. Subjects at risk can be identified according to the methods described herein or according to methods known to practitioners in the art. Typically, the subject is in the first or second trimester of pregnancy. In certain embodiments, the subject is in the first 20 weeks of pregnancy. In certain embodiments, the subject is in the first or second months of pregnancy. In certain embodiments, the methods will be administered before pregnancy is achieved.

Another aspect of the present invention provides methods of treating or preventing preeclampsia and preterm labor by administering to a subject in need thereof an effective amount of GCSF or an effective amount of mobilized peripheral blood stem cells. The methods can be administered to any female subject at risk for preeclampsia or preterm labor. Subjects at risk can be identified according to the methods described herein or according to methods known to practitioners in the art. Typically, the subject is in the second or third trimester of pregnancy.

DETAILED DESCRIPTION

The practice of the present invention will employ, unless otherwise indicated, conventional methods of molecular biology, cell biology, immunology, biochemistry, microbiology, gynecology and obstetrics within the skill of the art. Such techniques are explained fully in the literature. All publications, patents and patent applications cited herein, whether supra or infra, are hereby incorporated by reference in their entirety.

DEFINITIONS

As used herein, the following terms shall have the following meanings:

The terms "treat", "treating" or "treatment" as used herein, refers to a method of alleviating or abrogating a disorder and/or its attendant symptoms. The terms "prevent", "preventing" or "prevention", as used herein, refer to a method of barring a subject from acquiring a disorder and/or its attendant symptoms. In certain embodiments, the terms "prevent", "preventing" or "prevention" refer to a method of reducing the risk of acquiring a disorder and/or its attendant symptoms.

The term "artificial insemination" refers to an assisted reproduction procedure where a donor's sperm is deposited into the vagina (intravaginal insemination), cervical canal (intracervical insemination), uterine cavity (intrauterine insemination), or fallopian tubes (intratubal insemination) of the recipient. Intrauterine insemination (IUD is a subset of artificial insemination in which sperm that have been washed of seminal fluid are placed directly into the uterus to bypass the vagina and cervix. Artificial insemination can be performed without any fertility drugs on the day of ovulation or can be performed using fertility drugs to stimulate superovulation (i.e., release of more than one oocyte per cycle).

The term "spontaneous abortion" refers to delivery or loss of the product of conception before the 20th week of pregnancy. The term spontaneous abortion includes but is not limited to miscarriage, threatened abortion, inevitable spontaneous abortion, incomplete spontaneous abortion, habitual or recurrent spontaneous abortion or missed abortion.

The term "miscarriage" is synonymous with spontaneous abortion.

The term "threatened spontaneous abortion" refers to any bleeding or cramping of the uterus in the first 20 weeks of pregnancy.

The term "inevitable spontaneous abortion" refers to bleeding or rupture of the membranes accompanied by pain and dilation of the cervix.

The term "incomplete spontaneous abortion" refers to expulsion of part of the products of conception or rupture of the membranes.

The term "habitual spontaneous abortion" or "recurrent spontaneous abortion" refers to three or more consecutive spontaneous abortions.

The term "missed abortion" refers to delay in expulsion of a dead fetus.

The term "assisted reproduction" refers to clinical and laboratory techniques used to enhance fertility in humans and animals, including, but not limited to, in vitro fertilization, FET, ICSI, GIFT, ZIFT, artificial insemination and the like.

The term "in vitro fertilization" refers to the procedure involving ovarian hyperstimulation (optionally), oocyte retrieval from the mother-to-be or a donor, fertilization outside the subject's body, embryo culture and embryo transfer. As used herein, embryo transfer refers to the procedure involving transfer to a subject's uterus, of the developing or cleaving embryos or pre-embryos, also termed preimplantation embryos.

The term "implantation failure" refers to the failure of an embryo produced by assisted reproduction or through artificial insemination to implant or to implant normally in the uterus of a recipient subject.

The term "preeclampsia" refers the development of hypertension with albuminuria or edema typically between the 20th week of pregnancy and the end of the first week postpartum. Any pregnant subject who develops a blood pressure of 140/90 mm Hg or higher, edema of the face or hands, albuminuria of ≧1+ or whose blood pressure rises by 30 mm Hg systolic or 15 mm Hg diastolic (even if less than 140/90 mm Hg) is considered preeclamptic.

The term "colony stimulating factor" or "CSF" relates to a growth factor that promotes and contributes to the maturity of cells, such as, hematopoietic and blood cells. Examples of CSF molecules include, but are not limited to, erythropoietin, G-CSF, GM-CSF, macrophage CSF, interleukin (IL)-3, IL-6 and stem cell factor.

The term "granulocyte-colony stimulating factor" or "G-CSF" refers to compounds or factors that stimulate proliferation, differentiation, commitment and end cell functional activation of granulocytes in an animal, including a human subject. G-CSF includes derivatives, mimetics, variants and chemically modified compounds or hybrids thereof as described in U.S. Pat. Nos. 5,399,345; 5,416,195; 5,981,551; 6,166,183 and 6,261,550, the contents of which are incorporated by reference in entireties. G-CSF is commercially available under the names Neupogen® (Amgen), Teva-grastim® (Teva), Biograstim® (CT Arzneimittel), Ratio-grastim® (Ratiopharm GmbH)), Zarzio® (Sandoz GmbH), Filgrastim Hexal® (Hexal AG), Neulasta® (Amgen), Granocyte® and Neutrogin® (Chugai), and Neu-up® (Kyowa Hakko).

The term "granulocyte" refers to a white blood cell containing granules, especially a leukocyte (white blood cell or corpuscle) containing neutrophil, basophil or eosinophil granules in its cytoplasm.

The term "granulocyte/macrophage colony stimulating factor" or "GM-CSF" refers to compounds or factors that stimulate proliferation, differentiation, commitment and end cell functional activation of monocytes and granulocytes in an animal, including a human subject. GM-CSF includes derivatives, mimetics, variants and chemically modified compounds or hybrids thereof as described in, for example, U.S. Pat. Nos. 5,895,646; 5,891,429 and 5,908,763; the contents of which are incorporated by reference in entireties. GM-CSF is commercially available under the trade names Leukine®, Berlex® and Leucomax® (Wyeth).

The term "macrophage colony stimulating factor" or "M-CSF" (also known as "CSF-1") refers to compounds or factors that stimulate proliferation or promote survival of monocytes and macrophages in an animal, including a human subject. M-CSF includes derivatives, mimetics, variants and chemically modified compounds or hybrids thereof as described in, for example, U.S. Pat. Nos. 5,837,230 and 5,888,495; the contents of which are incorporated by reference in entireties. M-CSF is commercially available under the trade name Leukoprol® (Kyowa).

The term "macrophage" relates to a mononuclear, phagocytic white blood cell that can exit the circulation and enter tissue spaces.

The term "therapeutically effective amount" refers to that amount of an active agent being administered sufficient to prevent development of or alleviate to some extent one or more of the symptoms of the condition or disorder being treated.

The term "preterm labor" also known as premature labor, refers to the beginning of regular contractions that cause the cervix to begin dilation and effacement before the 37th week of pregnancy.

The term "effective amount" refers to that amount of an active agent being administered sufficient to prevent the disorder or prevent one or more symptoms of the disorder being treated. In certain embodiments, the term "effective amount" refers to that amount of an active agent being administered sufficient to reduce the risk of the disorder or one or more symptoms of the disorder.

The term "subject" refers to animals such as mammals, including, but not limited to, primates (such as humans), cows, sheep, goats, horses, dogs, cats, rabbits, rats, mice and the like. In preferred embodiments, the subject is a human female.

The term "label" refers to a display of written, printed or graphic matter on the immediate container of an article, for example the written material displayed on a vial containing a pharmaceutically active agent.

The term "labeling" refers to all labels and other written, printed or graphic matter on any article or any of its containers or wrappers or accompanying such article, for example, a package insert or instructional videotapes or computer data storage devices, such as CDs and DVDs, accompanying or associated with a container of a pharmaceutically active agent.

The present invention is directed to methods of preventing spontaneous abortion and implantation failure, and methods of treating or preventing preeclampsia and preterm labor described in detail below.

Methods for Preventing or Reducing the Likelihood of Implantation Failure and Miscarriage in a Recipient of Artificial Insemination by Administration of G-CSF In one aspect, the present invention provides methods of preventing or reducing the likelihood of embryo implantation failure and miscarriage in recipients of artificial insemination and particularly in recipients of intrauterine insemination during assisted reproduction by administrating to a subject in need thereof an effective amount of G-CSF.

Artificial insemination (AI) involves depositing a donor's sperm into the vagina, cervical canal, uterine cavity, or fallopian tubes of the recipient. Intrauterine insemination (IUD is a subset of artificial insemination in which sperm that have been washed of seminal fluid are placed directly into the uterus to bypass the vagina and cervix. IUI can be performed without any fertility drugs on the day of ovulation or can be performed using fertility drugs to stimulate superovulation (i.e., release of more than one oocyte per cycle).

According to many published studies, insemination combined with controlled ovarian stimulation (COH) provides better pregnancy rates. COH is most often achieved using clomiphene citrate and human chorionic gonadotropin (HCG) to trigger superovulation. Insemination is performed within 2 days of HCG administration. Alternatively, COH can be achieved using purified or recombinant follicle stimulation hormone with or without recombinant or purified luteinizing hormone. Again, this is followed by administration of HCG to trigger superovulation.

In a typical AI procedure, the recipient usually is stimulated with medication to stimulate multiple egg development and the insemination is timed to coincide with ovulation-release of the eggs from the follicles.

On the day of the procedure, a semen specimen is harvested and "washed" in the laboratory (called sperm processing or sperm washing). By this process, the sperm is separated from the other components of the semen and concentrated in a much smaller volume. Various media and techniques can be used to perform the washing and separation, depending on the specifics of the individual case and preferences of the fertility doctor and laboratory. The sperm processing takes about 20-60 minutes, depending on the technique utilized.

A speculum is placed in the vagina and the cervical area is gently cleaned. Then the separated and washed specimen consisting of a purified fraction of highly motile sperm is placed either in the vagina (intravaginal insemination, WI), cervix (intracervical insemination, ICI), higher in to the uterine cavity (intrauterine insemination, IUD, or fallopian tubes (intrafallopian insemination, IFI) using a sterile, thin and soft catheter. Intrauterine insemination has a better success rate than intracervical insemination. Therefore, it is the preferred method at some fertility specialist centers and some general obstetrical practices.

While not intending to be bound by any particular theory of operation, it is believed that a significant percentage of implantation failure and miscarriage during artificial insemination is caused by or associated with inappropriate immune responses in the recipient of the artificial insemination. In particular, it is believed that subjects at risk for embryo implantation failure or miscarriage present with an overproduction of T-helper 1 (Th1) cytokines and underproduction of T-helper 2 (Th2) cytokines. Positive correlations in human and animal models have been demonstrated, (see, Kwak-Kim et al., 2003, Human Reproduction 18:767-73, Krishnan et al., 1996, J. Immunol. 156:653-62) but remain controversial (see, Chaouat et al., 2003, J. Reproductive Immunol. 59:205-17). The Th1 cytokine associated with overproduction can be interferon-γ (INF-γ). The Th2 cytokines associated with underproduction can be interleukins 10 and 4 (IL-10 and IL-4).

To prevent or reduce the likelihood of implantation failure, the G-CSF is typically administered before the insemination procedure. The administration is continued until implantation of the embryo to the uterine wall is achieved, until the risk of failed implantation is reduced or eliminated, or according to the judgment of a practitioner of skill in the art.

In certain embodiments, the administration is continued until pregnancy is confirmed. In certain embodiments, G-CSF is administered daily for 1-35 consecutive days. In other embodiments, G-CSF is administered daily until the end of first trimester. In certain embodiments the administration is started before the time of controlled ovarian hyperstimulation or about the time of controlled ovarian hyperstimulation, and continued daily until about 3 days, about 5 days, about 7 days, about 10 days, about 12 days, about 14 days, about 30 days, about 45 days, or about 60 days after insemination into the subject's vagina, cervix, uterus, or fallopian tubes. In certain embodiments, the administration is started about 14 days, 7 days, 5 days, 3 days, and 1 day before insemination into the subject's vagina, cervix, uterus, or fallopian tubes. In another embodiment, the administration is started about the time of controlled ovarian hyperstimulation and continued daily until about the end of the first trimester. In another embodiment, the dose is administered for five consecutive days about the time of insemination and continued daily until about 3 days, about 5 days, about 7 days, about 10 days, about 12 days, about 14 days, about 30 days, about 45 days, or about 60 days after insemination into the subject's vagina, cervix, uterus, or fallopian tubes. In certain embodiments, the administration is continued daily until the subject presents a normal Th1 immune response or a normal Th2 immune response or both, according to the judgment of a practitioner of skill in the art.

In certain embodiments, an effective amount of G-CSF is administered to a subject at risk of implantation failure or miscarriage. In certain embodiments, a subject at risk is a subject that has failed one or more artificial insemination procedures. In further embodiments, a subject at risk is a subject undergoing her first AI procedure. In further embodiments, the subject can also be in any other population at risk for failed embryo implantation or miscarriage as determined by a practitioner of skill in the art. In another embodiment, the subject has had one or more previous spontaneous abortions. Other subjects at risk include those with unusually high Th1 immune responses or unusually low Th2 immune responses. In further embodiments, the subject can also be in any other population at risk for failed embryo implantation or miscarriage as determined by a practitioner of skill in the art.

In certain embodiments, the G-CSF is administered to the subject prior to insemination. For instance, the G-CSF is administered to a subject that is planning or attempting to become pregnant via artificial insemination. Thus, the G-CSF can be administered to the mother-to-be during the controlled ovarian hyperstimulation procedure or prior to the insemination if no controlled ovarian hyperstimulation procedure is used. The G-CSF can be administered at any time during the artificial insemination process.

The G-CSF treatment may also be used to prevent or reduce the likelihood of implantation failure or miscarriage in recipients of other assistant reproductive procedures, such as in vitro fertilization (IVF), frozen embryo transfer (FET), intracytoplasmic sperm injection (ICSI), zygote intrafallopian transfer (ZIFT), and gamete intrafallopian transfer (GIFT).

In vitro fertilization is an assisted reproduction procedure to overcome fertility problems caused by, for example, tubal disease, endometriosis, oligospermia, sperm antibodies and unexplained infertility. The procedure can include controlled ovarian hyperstimulation with "fertility drugs" such as ovarian stimulants like clomiphene citrate and gonadotropin-releasing hormones. Hyperstimulation of the ovaries can induce growth of the egg (oocyte) and its encasing cells, collectively also termed the ovarian follicles. After sufficient follicular growth, final follicular maturation is induced and oocytes are retrieved or harvested. The oocytes are fertilized in vitro with sperm and the embryos cultured. A small number of embryos, generally 2-4, are then transferred to the uterus. Despite the transfer of multiple embryos, the term pregnancy rate is only about 25%.

Frozen embryo transfer (FET) is a procedure that utilizes cryopreserved embryos from a previous cycle of in vitro fertilization or ICSI. The cryopreserved embryos are thawed and transferred into the uterine cavity through a catheter. FET can be done with no medications or with the use of various medications including estrogen and progesterone.

Intracytoplasmic sperm injection (ICSI) involves placing a sperm inside an egg with a microscopic needle, rather than placing many sperm close to the outside of the egg, as in IVF, in a dish in a lab. Once fertilization occurs, the resulting embryo is placed in the recipient's uterus.

Gamete intrafallopian transfer (GIFT) is a procedure that combines eggs and sperm in a dish in a lab. The egg/sperm mixture is then surgically injected into the recipient's fallopian tubes using a laparoscope or fiber-thin tube. Fertilization happens inside the recipient's body, and the embryo implants naturally. Although this procedure was once commonly practiced, it's rarely used today because the success with IVF is far greater on average.

To prevent or reduce the likelihood of implantation failure or miscarriage, the G-CSF is typically administered before the assisted reproduction procedures. The administration is continued until implantation of the embryo to the uterine wall is achieved, until the risk of failed implantation or miscarriage is reduced or eliminated, or according to the judgment of a practitioner of skill in the art.

In certain embodiments, the administration is started before eggs, sperm, or embryos are transferred into the recipient. In certain embodiments, the administration is continued until pregnancy is confirmed. In certain embodiments, the administration is started about the time of controlled ovarian hyperstimulation and continued until about 3 days, about 5 days, about 7 days, about 10 days, about 12 days, about 14 days, about 30 days, about 45 days, or about 60 days after the transfer of embryo to the subject's uterus. In certain embodiments, the administration is started about the time of controlled ovarian hyperstimulation and continued until about the end of the first trimester. In another embodiment, the dose is administered for five consecutive days about the time of embryo/gamete transfer. In certain embodiments, the administration is continued until the subject presents a normal Th1 immune response for a pregnant subject or a normal Th2 immune response for a pregnant subject or both, according to the judgment of a practitioner of skill in the art.

In certain embodiments, the retrieved oocytes or embryos are maintained and cultured in medium containing G-CSF prior to their transfer to the uterus of the recipient.

Methods of Preventing Spontaneous Abortion with G-CSF

Another aspect of the present invention provides methods of preventing or reducing the likelihood of spontaneous abortion by administering to a subject in need thereof an effective amount of a G-CSF.

While not intending to be bound by any particular theory of operation, it is believed that many instances of spontaneous abortion and recurrent spontaneous abortion are caused or associated with inappropriate immune responses in a pregnant subject. In particular, it is believed that these subjects at risk for spontaneous abortion and recurrent spontaneous abortion present inappropriate immune cytokines associated with a T-helper 1 (Th1) immune response known to those of skill in the art. (See, Kwak-Kim et at, 2003, Hum. Reprod. 18(4): 676-773.) In contrast, subjects that have healthy pregnancies typically present immune cytokines associated with a T-helper 2 (Th2) immune response. It is believed that administration of G-CSF can reduce the inappropriate Th1 response and/or increase a T-helper 2 (Th2) immune response in a subject. This invention is thus based, in part, on the discovery that administration of G-CSF can shift a subject's immune response towards a healthy Th2 response during pregnancy and thereby reduce or eliminate the risk of spontaneous abortion.

The subject can be any mammalian subject at risk for a spontaneous abortion. In particularly preferred embodiments, the subject is a human female. In certain embodiments, the subject has previously had one or more spontaneous abortions. In further embodiments, the subject has previously had two or more spontaneous abortions. In other embodiments, the subject has had recurrent spontaneous abortions, i.e., three or more spontaneous abortions.

In further embodiments, the subject can be any subject in a population at risk for spontaneous abortion. For instance, the subject can be a human female in an age group at risk for spontaneous abortion. In particular embodiments, the subject can be a human female greater than 35 years of age, greater than 40 years of age or greater than 45 years of age. In other particular embodiments, the subject can be a human female less than 20 years of age or less than 15 years of age. However, essentially a woman of any age that presents with a reproductive infirmity, such as spontaneous abortion, preeclampsia and preterm labor, is a candidate for obtaining the materials and methods of the instant invention.

In further embodiments, the subject can also be in any other population at risk for spontaneous abortion as determined by a practitioner of skill in the art. In certain embodiments, the subject is threatening abortion. In other embodiments, the subject is obese, morbidly obese, has overall poor health or comorbid conditions that indicate a risk of spontaneous abortion to the skilled practitioner. In certain embodiments, these conditions can be incompetent cervix, uterine anomalies, hypothyroidism, diabetes mellitus, chronic nephritis, acute infection, use of illicit drugs (such as cocaine or crack), immunologic problems, severe emotional shock and viral infection (especially cytomegalovirus, herpes virus and rubella) (see Merck Manual 17th edition, 1999, Merck Research Laboratories, Whitehouse Station, N.J., p. 2053). In certain embodiments, the subject has had an implantation failure during a previous assisted reproduction procedure. Other subjects at risk include those with unusually high Th1 immune responses or unusually low Th2 immune responses. In further embodiments, the subject can also be in any other population at risk for spontaneous abortion as determined by a practitioner of skill in the art.

In certain embodiments, the G-CSF is administered to the subject prior to pregnancy. For instance, the G-CSF is administered to a subject that is planning or attempting to become pregnant. In other embodiments, the G-CSF is administered to a pregnant subject. The G-CSF can be administered at any time during the first or second trimester of pregnancy. In preferred embodiments, the G-CSF is administered during the first 20 weeks of pregnancy. In other embodiments, the G-CSF is administered to a subject who is pregnant or attempting to become pregnant through artificial insemination or natural conception.

Methods for Treating or Preventing Preeclampsia or Preterm Labor with GCSF

In a further aspect, the present invention provides methods of treating or preventing preeclampsia or preterm labor by administering to a subject in need thereof an effective amount of granulocyte colony stimulating factor.

While not intending to be bound by any particular theory of operation, it is believed that preeclampsia and preterm labor is caused or associated with inappropriate immune responses in a pregnant subject. In particular, it is believed that subjects at risk for preeclampsia or preterm labor present inappropriate immune cytokines associated with a T-helper 1 (Th1) immune response known to those of skill in the art. In contrast, subjects that have healthy pregnancies typically present immune cytokines associated with a T-helper 2 immune response. It is believed that administration of GCSF can reduce the inappropriate Th1 response and/or increase a Th2 immune response in a subject. This invention is thus based, in part, on the discovery that administration of GCSF can shift a subject's immune response towards a healthy Th2 response during pregnancy and thereby treat or prevent preeclampsia or preterm labor.

In the methods of treatment, GCSF is administered to a subject presenting one or more signs or symptoms of preeclampsia or preterm labor. The subject can be any subject that presents any of the signs or symptoms of preeclampsia during pregnancy such as hypertension, swelling or edema and excessive protein in the urine. For example, the subject can be any subject that develops hypertension with albuminuria or edema between the 20th week of pregnancy and the end of the 1st week postpartum. Particular subjects include pregnant females who develop a blood pressure of 140/90 mm Hg, edema of the face or hands or albuminuria of ≧1+ or whose blood pressure rises by 30 mm Hg systolic or 15 mm Hg diastolic (even if less than 140/190 mm Hg) between the 20th week of pregnancy and the end of the 1st week postpartum. Particularly preferred subjects are human females.

In the methods of treatment, the GCSF is typically administered until the signs or symptoms of preeclampsia or preterm labor are alleviated or reduced as long as the therapeutic benefit outweighs the risk of adverse events according to the judgment of a practitioner of skill in the art. The dosing can continue as long as the subject displays no toxic effects of the administration according to the judgment of a practitioner of in the art. In certain embodiments, the treatment is continued until the subject presents a normal Th1 immune response for a pregnant subject or a normal Th2 response for a pregnant subject, or both, according to the judgment of a practitioner of skill in the art.

In the methods of prevention, GCSF is administered to a subject at risk for developing preeclampsia or preterm labor. The subject can be any mammalian subject at risk for preeclampsia or preterm labor. Subjects at risk include subjects carrying multiple babies, subjects younger than age 20 and subjects older than age 40. Further subjects include those pregnant for the first time (primigravida), subjects with preexisting hypertension and subjects with preexisting vascular disease. Other subjects at risk include those with unusually high Th1 immune responses or unusually low Th2 immune responses. In particularly preferred embodiments, the subject is a human female.

In the methods of prevention, GCSF is administered as long as the subject is at risk for preeclampsia and as long as the therapeutic benefit outweighs the risk of adverse events and also, so long as no toxicity is observed according to the judgment of a practitioner of skill in the art. In certain embodiments, GCSF is administered for the duration of the pregnancy. In particular embodiments, administration is provided in the 2nd and 3rd trimester of pregnancy. In further embodiments, administration is continued after delivery for about one, about two, about three, about four, about five, about six, about seven or about eight weeks post partum. In certain embodiments, the treatment is continued until the subject presents a normal Th1 immune response for a pregnant subject or a normal Th2 immune response for a pregnant subject, or both, according to the judgment of a practitioner of skill in the art.

The GCSF can be administered according to any method of administration known to those of skill in the art. Preferred methods of administration include subcutaneous administration. Other effective modes of administration are described in detail in the sections below.

G-CSF and Formulation

As described in detail above, the present invention provides methods of administering an effective amount of granulocyte colony stimulating factor (G-CSF) to prevent or reduce the likelihood of spontaneous abortion, implantation failure and miscarriage during and following artificial insemination.

The G-CSF administered in the methods of the invention can be any G-CSF known to one of skill in the art without limitation. Thus, a range of modifications can be made to the wild-type G-CSF molecules so long as the known immune system modulating activity of the G-CSF is maintained. There are a number of assays that can be used to ensure that any one modified G-CSF retains the desired immune system modulating activity. Plural types of G-CSF molecules can be administered in the practice of the instant invention. The plural G-CSF molecules can be administered concurrently, consecutively, or sequentially. In certain embodiments, the G-CSF can be any G-CSF or any derivative, variant, mimetic, chemically modified version or hybrid thereof, as described in U.S. Pat. Nos. 5,399,345; 5,416,195; 5,981,551; 6,166,183 and 6,261,550, the contents of which are hereby incorporated by reference in their entireties. In further embodiments, the G-CSF can be administered in the form of a nucleotide sequence encoding G-CSF or expression vectors encoding G-CSF described in U.S. Pat. No. 5,422,248, the content of which is hereby incorporated by reference in its entirety. The G-CSF can be formulated according to any formulation for administration known to those of skill in the art.

In certain embodiments, the G-CSF is a commercially available G-CSF available as a pharmaceutical composition, suitable for administration to an animal, including a human. Such commercially available pharmaceutical compositions can be, for example, filgrastim (Neupogen® (Amgen), Tevagrastim® (Teva), Biograstim® (CT Arzneimittel), Ratiograstim® (Ratiopharm GmbH), Zarzio® (Sandoz GmbH), Filgrastim Hexal® (Hexal AG), pegfilgrastim (Neulasta®, Amgen), nartograstim (Neu-Up®, Kyowwa) or lenograstim (Neutrogin®, Granocyte®, Chugai).

Filgrastim, nartograstim, and lenograstim are useful for promoting neutrophil proliferation and are generally administered to individuals in need to increased neutrophils, for example, patients undergoing chemotherapy. Filgrastim, nartograstim, and lenograstim are indicated for myelosuppressive chemotherapy, bone marrow transplant, peripheral blood progenitor cell collection and severe chronic neutropenia. Off label uses include treatment of neutropenia in AIDS patients, aplastic anemia, hairy cell leukemia, myelodysplasia, drug-induced and congenital agranulocytosis and alloimmune neo-natalneutropenia.

The usual treatment of neutropenia associated with myelosuppression is 5 mcg/kg/day, once daily either by bolus subcutaneously or short (15-30 minute) intravenous infusion or by continuous subcutaneous or intravenous infusion. Administration is once daily starting no earlier than 24 hours after chemotherapy and continues for 14 days or until the individual's absolute neutrophil count is 10,000/mm3. For patients undergoing bone marrow transplant, the usual dose is 10 mcg/kg/day administered as an intravenous infusion over 4-24 hours or as a continuous 24 hour subcutaneous infusion. The first dose is generally administered at least 24 hours after chemotherapy and at least 24 hours after bone marrow infusion. During recovery, the dose is adjusted according to the patient's absolute neutrophil count. Filgrastim dosing for peripheral blood progenitor cells generally begins at 10 μg/kg/day subcutaneously either as a bolus or continuous infusion. It is recommended that filgrastim be given for at least four days before leukapheresis and continued until the last leukapheresis procedure. Doses of filgrastim for congenital neutropenia are 5 mcg/kg subcutaneously twice daily while idiopathic or cyclic neutropenia is generally treated with a dose of 5 mcg/kg subcutaneously once daily.

Pegfilgrastim is a monomethoxypolyethylene glycol conjugate of filgrastim. The pharmaceutical composition is commercially available as preservative free solutions of 10 mg/ml pegfilgratim in prefilled single-dose syringes. Pegfilgrastim is indicated to decrease infections in patients with febrile neutropenia undergoing myelosuppressive chemotherapy. Recommended dosing is a single 6 mg subcutaneous injection administered once per chemotherapy cycle.

In the above-described methods, G-CSF is administered in an effective amount, i.e., an amount effective to reduce or eliminate the risk of implantation failure or spontaneous abortion. The amount can be determined by the skilled practitioner guided by the description herein and the knowledge in the art. In preferred embodiments, the amount can be any amount of G-CSF that reduces the Th1 response of the subject. In further embodiments, the amount can be any amount sufficient to increase or initiate a Th2 response in the subject. Assays to determine Th1 and Th2 responses in the subject are well known to those of skill in the art (See e.g., Schust and Hill, 1996, J. Soc. Gynecol Investig. 3:259-61, Xing et al., 2001, Chin. Med. J. 114:921-4, Raghupathy et al., 1999, Cell Immunol. 196:122-30, Mauri et al., 1996, J. Immunol. 26:1511-8, Doncorli et al., 1997, Eur. J. Imm. 27:1451-8, Raziuddin, 1998, J. Rheumatol 25:329-33, Moverare et al., 2000, Allergy 55:171-5). In particular embodiments, G-CSF is administered at doses of about 0.1 mcg/kg/day to 600 mcg/kg/day, 0.5 mcg/kg/day to 300 mcg/kg/day, 1 mcg/kg/day to 100 mcg/kg/day, 1 mcg/kg/day to 50 mcg/kg/day, 1 mcg/kg/day to 20 mcg/kg/day, 1 mcg/kg/day to 10 mcg/kg/day, 1 mcg/kg/day to 2 mcg/kg/day; and about 1.67 mcg/kg/day. In another embodiment, at least 0.01 mg, at least 0.02 mg, at least 0.05 mg at least 0.1 mg, at least 0.2 mg, at least 0.5 mg, at least 1 mg, at least 2 mg, at least 5 mg, at least 10 mg, at least 25 mg, at least 50 mg, at least 75 mg, at least 100 mg, at least 125 mg, at least 150 mg, at least 175 mg, at least 200 mg, at least 300 mg, at least 600 mg or more is administered daily.

In certain embodiments described above, the present invention provides methods of administering to a subject in need thereof an effective amount of G-CSF as monotherapy. In other embodiments, the present invention provides methods of administering to a subject an effective amount of G-CSF in combination with at least one additive. Additives include cytokines that suppress Th1 immune response, cytokines that enhance Th2 immune response, and non-myeloablative immunosuppressive agents. Additives may also include cytokines that support successful pregnancy outcome through non-immunologic mechanisms such as stimulation of trophoblast cell proliferation, inhibition of trophoblast cell apoptosis, stimulation of trophoblasat invasion, or stimulation of angiogenesis. Additives may also include anti-inflammatory agents, and inhibitors of pro-inflammatory cytokines.

Examples of additives include, but are not limited to, interferon alpha, interferon beta, macrophage colony stimulating factor (M-CSF), granulocyte macrophage colony stimulating factor (GM-CSF), leukemia inhibitory factor (LIF), transforming growth factor beta (TGF-beta), interleukin-1(IL-1), IL-3, IL-4, IL-6, IL-7, IL-8, IL-9, IL-10, IL-11, IL-13, IL-14, IL-15, IL-19, IL-20, IL-21, IL-22, IL-24, IL-25, IL-26, IL-27, IL-28, IL-29, IL-30, IL-31, IL-32, IL-33, and IL-35.

In certain embodiments, additives may include inhibitors of pro-inflammatory cytokines such as, but not limited to, anti-TNF-alpha, pentoxifyllin, anti-VEGF, anti-CD28, anti-CD80, anti-CD86, anti-CD40L, and the like.

Other additives that may be used with a G-CSF include anti-inflammatory agents. The anti-inflammatory agent can be one that reduces leukocyte populations or inhibits leukocyte function. Other anti-inflammatory agents can be used as well. For example, vitamin D3 (1,25-dihydroxycholecalciferol) and analogs thereof can be used. In another example, corticosteroids such as prednisone or methylprednisolone can be used.

Other additives that may be used with a G-CSF are those currently used to treat recurrent spontaneous abortion, miscarriage, or implantation failure, such as intravenous Ig and heparin.

The additive can be another CSF, erythropoietin or stem cell factor. The CSF can be G-CSF, GM-CSF or macrophage CSF.

The G-CSF can be administered according to any method of administration known to those of skill in the art. Preferred methods of administration include subcutaneous administration, parenteral administration, enteral administration, topical administration. G-CSF may also be administered by inhalation. In the compositions administered, the G-CSF can be formulated in any manner known to those of skill in the art for formulating and administering effective amounts of G-CSF.

Filgrastim or non-glycosylated G-CSF is available as a preservative-free pharmaceutical composition comprising 300 mcg/ml and 480 mcg/ml vials or 300 mcg/0.5 ml and 480 mcg/0.5 ml self-injectors. The composition can be administered subcutaneously without further admixture. Intravenous preparations require dilution with proper diluent, such as 5% dextrose, diluted to a final concentration of filgrastim of 5 to 15 mcg/ml. Saline is not recommended as a diluent due to product precipitation. Mixture with albumin is recommended to prevent adsorption to plastic or glass materials during preparation and infusion. The final concentration of human albumin should be 2 mg/ml. It is highly recommended that filgrastim be refrigerated at 2° to 8° C.

The presently available pharmaceutical composition contains a small amount of acetate, Tween 80, sodium, and sorbitol. These excipients are used to achieve and maintain characteristics that are physiologically acceptable to the body and pharmaceutically practical. Such characteristics include tonicity, osmoticity, osmolality, osmolarity, viscosity and shelf life. Aqueous pharmaceutical compositions of G-CSF with increased serum half life have been described, for example, in U.S. Pat. No. 5,919,757, incorporated herein by reference in its entirety.

The pharmaceutical compositions can comprise the G-CSF in a salt form. For example, because proteins can comprise acidic and/or basic termini side chains, the proteins can be included in the pharmaceutical compositions in either the form of free acids or bases, or in the form of pharmaceutically acceptable salts. Pharmaceutically acceptable salts can include, suitable acids which are capable of forming salts with the proteins of the present invention including, for example, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, cinnamic acid, anthranilic acid, citric acid, naphthalene sulfonic acid, sulfanilic acid and the like. Suitable bases capable of forming salts with the subject proteins can include, for example, inorganic bases such as sodium hydroxide, ammonium hydroxide, potassium hydroxide and the like; and organic bases such as mono-, di- and tri-alkyl amines (for example, triethyl amine, diisopropyl amine, methyl amine, dimethyl amine and the like) and optionally substituted ethanolamines (for example, ethanolamine, diethanolamine and the like).

Although commercially available G-CSF is currently administered subcutaneously or intravenously, any method of administration that provides a therapeutically effective amount of G-CSF can be used in the methods of the invention. In one aspect, G-CSF can be in a variety of forms suitable for any route of administration, including, but not limited to, parenteral, enteral, topical or inhalation.

Parenteral administration refers to any route of administration that is not through the alimentary canal, including, but not limited to, injectable administration, i.e., intravenous, intramuscular and the like as described below. Enteral administration refers to any route of administration which is oral, including, but not limited to, tablets, capsules, oral solutions, suspensions, sprays and the like, as described below. For purposes of this invention, enteral administration also refers to rectal and vaginal routes of administration. Topical administration refers to any route of administration through the skin, including, but not limited to, creams, ointments, gels and transdermal patches, as described below (see also, Pharmaceutical Sciences, 18th Edition (Gennaro et al., eds., Mack Printing Company, Easton, Pa., 1990).

Parenteral pharmaceutical compositions of the present invention can be administered by injection, for example, into a vein (intravenously), an artery (intraarterially), a muscle (intramuscularly) or under the skin (intradermally or subcutaneously) or in a depot composition.

Injectable pharmaceutical compositions can be sterile suspensions, solutions or emulsions of the G-CSF in aqueous or oily vehicles. The compositions can also comprise formulating agents or excipients, such as suspending, stabilizing and/or dispersing agents. The formulations for injection can be presented in unit dosage form, in ampules or in multidose containers, and can comprise added preservatives. In certain embodiments, the pharmaceutical compositions contain buffers such as citrate, acetate, phosphate, tris (hydroxymethyl) amino methane or THAM (tromethamine).

Depot or sustained release pharmaceutical compositions can be used in the methods of the invention. For example, continuous release of G-CSF can be achieved by the conjugation of the G-CSF with a water soluble polymer as described in U.S. Pat. No. 5,320,840. G-CSF may be contained in an inert matrix or device for slow release after implantation of the matrix or device.

Injectable pharmaceutical compositions can be pharmaceutically appropriate compositions for any route of injectable administration, including, but not limited to, intravenous, intrarterial, intracoronary, pericardial, perivascular, intramuscular, subdermal, subcutaneous and intraarticular.

Alternatively, the injectable pharmaceutical composition can be provided in powder form for reconstitution with a suitable vehicle, including but not limited to sterile pyrogen free water, buffer, dextrose solution, etc., before use. To this end, the G-CSF can be lyophilized as appropriate. The pharmaceutical compositions can be supplied in unit dosage forms and reconstituted prior to use in vivo.

For prolonged delivery, the pharmaceutical composition can be provided as a depot preparation, for administration by implantation; e.g., subcutaneous, intradermal, or intramuscular injection. Thus, for example, the pharmaceutical composition can be formulated with suitable polymeric or hydrophobic materials as an emulsion in an acceptable oil or ion exchange resins, or as sparingly soluble derivatives; as a sparingly soluble salt form of the G-CSF, or derivative, mimetic or variant thereof. The G-CSF can be present in an inert matrix or device for implantation to achieve prolonged release.

Alternatively, transdermal delivery systems manufactured as an adhesive disc or patch that slowly releases the active ingredient for percutaneous absorption can be used. To this end, permeation enhancers can be used to facilitate penetration of the G-CSF. A particular benefit may be achieved by incorporating the G-CSF into a transdermal patch.

For oral administration, the pharmaceutical formulations can take the form of, for example, tablets or capsules prepared by conventional means with pharmaceutically acceptable excipients such as binding agents (e.g., piegelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art (see, Remington's Pharmaceutical Sciences, 18th edition (Gennaro et al., eds.) Mack Printing Company, Pa., 1990).

Liquid pharmaceutical compositions for oral administration can take the form of, for example, solutions, syrups or suspensions, or they can be a dry product for constitution with water or other suitable vehicle before use. Such liquid pharmaceutical compositions can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid).

The pharmaceutical compositions can also comprise buffer salts, flavoring, coloring and sweetening agents as appropriate. Pharmaceutical compositions for oral administration can be suitably prepared to provide controlled release of the G-CSF.

Enteral pharmaceutical compositions can be suitable for buccal administration, for example, in the form of tablets, troches or lozenges. For rectal and vaginal routes of administration, the G-CSF can be prepared as solutions (e.g. for retention enemas), suppositories or ointments. Enteral pharmaceutical compositions can be suitable for admixture in feeding mixtures, such as, for mixture with total parenteral nutrition (TPN) mixtures or for delivery by a feeding tube (see, Dudrick et al., 1998, Surg. Technol. Int. VII:174-184; Mohandas et al., 2003, Natl. Med. J. India 16(1):29-33; Bueno et al., 2003, Gastrointest. Endosc. 57(4):536-40; Shike et al., 1996, Gastrointest. Endosc. 44(5):536-40).

For administration by inhalation, the G-CSF can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of e.g., gelatin for use in an inhaler or insufflator can be formulated comprising a powder mix of the compound and a suitable powder base such as lactose or starch. Inhaled pharmaceutical compositions can be those, for example, described in U.S. Pat. Nos. 5,284,656 and 6,565,841, incorporated herein by reference in their entirety.

The compositions can, if desired, be presented in a pack or dispenser device that can comprise one or more unit dosage forms comprising the G-CSF. The pack can, for example, comprise metal or plastic foil, such as a blister pack. The pack or dispenser device can be accompanied by instructions for administration.

The pharmaceutical compositions can be for a single, one time use or can contain antimicrobial excipients, rendering the composition suitable for multiple, extended use with greater shelf stability; for example, a multi-use bottle. In another embodiment, the pharmaceutical composition of interest can be in unit dose or unit-of-use packages. As known in the art, a unit dose is targeted for a single use. The unit dose form can be in a vial, which can contain a solution or a desiccated form for reconstitution, a pre-filled syringe, a transdermal patch and the like.

As is known to those of skill in the art, a unit-of-use package is a convenient prescription size, patient ready unit labeled for distribution by health care providers. The package contains as much active ingredient as necessary for a typical treatment regimen.

The pharmaceutical composition can be labeled and have accompanying labeling to identify the composition contained therein and other information useful to health care providers and end users. The information can include instructions for use, dose, dosing interval, duration, indication, side effects and other contraindications, warnings, precautions, storage recommendations and the like.

Various embodiments of the pharmaceutical compositions have been described. The descriptions and examples are intended to be illustrative of the invention and not limiting. Indeed, it will be apparent to those of skill in the art that modifications to the pharmaceutical compositions can be made to the various embodiments of the invention described without departing from the spirit of the invention.

In one aspect the G-CSF compositions can be administered parenterally, for example, subcutaneously or intravenously. The parenteral administration can be in a single bolus or as a continuous infusion. In one aspect, the parenteral administration can be a single intravenous infusion given over 15-30 minutes. In another aspect the parenteral administration can be a continuous infusion of G-CSF diluted in 5% dextrose.

The methods provide for administration of G-CSF for a therapeutically or prophylactically effective time. In certain embodiments, the G-CSF is administered prior to the onset or observation of the disorder or symptoms accompanying the disorder. In further embodiments, the G-CSF is administered during the disorder or during the time period that symptoms accompanying the disorder are observed. In other embodiments, the G-CSF is administered for a time after the disorder had cleared. For example, the G-CSF can be administered about one day, about two days, about three days, about four days, about one week, about two weeks and up to about eight weeks, following resolution of threatened abortion or after confirmation of pregnancy during assisted reproduction.

Diagnostic Assays

While generally a medical history will serve to ascertain candidate subjects in need of treatments as described above, diagnostic assays can be used to ascertain subjects presented with reproductive inefficiencies that are correlated with particular immunologic parameters. As noted herein, patients with repeated spontaneous abortion, miscarriage, or implantation failure and the like present with particular profiles of their immune system status. Thus, subjects with high Th1 cell number or cell activity and/or reduced Th2 cell number or cell activity, or an aberrant ratio of the two may be candidates for obtaining the above-described treatment.

Hence, a diagnostic assay of interest is one that determines whether Th1 cell number or cell activity is enhanced. Another assay of interest is one that determines whether Th2 cell number or activity is decreased. Yet another assay of interest is one that determines a higher ratio of Th1 cell number to Th2 cell number, or Th1 cell activity to Th2 cell activity.

A number of known assays, for example, immunoassays or bioassays, can be used to make such determinations. For example, γ interferon, tumor necrosis factor alpha, tumor necrosis factor β, IL-2, IL-12, and IL-18 are markers of Th1 cells. Thus, assays for one or more of such cell-specific markers can provide the basis to conclude a higher than normal Th1 status. As to Th2, IL-4, IL-5, IL-6, IL-10 and IL-13 are known markers of that cell type. Thus, assays for one or more of such cell-specific markers can provide the basis to conclude a higher than normal Th2 status.

Diagnostic assays can be also used to ascertain subjects presenting with reproductive inefficiencies that are correlated with particular pathopysiologic parameters. Pathophysiologic markers could include markers of cell stress such as heat shock proteins, markers of oxidative stress such as nitric oxide and free radicals, markers of cell injury such as hepatic transaminases and creatine kinase, and markers of cell death including caspase 1 & 3.

In other embodiments, a diagnostic kit can be used to ascertain subjects presenting with reproductive inefficiencies that are correlated with serum or ovarian follicular fluid G-CSF concentrations. Such a kit would serve as a theranostic complimenting G-CSF as a therapeutic.

Kits

In another aspect, the present invention provides kits for carrying out the methods of the invention. In certain embodiments, the present invention provides kits for preventing or reducing the likelihood of spontaneous abortion or implantation failure during and following artificial insemination The kits comprise one or more effective doses of G-CSF along with a label or labeling with instructions on using the G-CSF to prevent or reduce the likelihood of spontaneous abortion or implantation failure during and following artificial insemination according to the methods of the invention. In certain embodiments, the kits can comprise components useful for carrying out the methods such as devices for delivering the G-CSF. In certain embodiments, the kit can comprise components useful for the safe disposal of devices for delivering the G-CSF, e.g., a sharps container for used syringes.

In other embodiments, the present invention provides kits for preventing or reducing the likelihood of spontaneous abortion and implantation failure in recipients of IVF, FET, ICSI, GIFT and ZIFT. The kits comprise one or more effective doses of G-CSF along with a label or labeling with instructions on using the G-CSF to prevent or reduce the likelihood of spontaneous abortion, miscarriage or implantation failure during and following IVF, FET, ICSI, GIFT and ZIFT. In certain embodiments, the kits can comprise components useful for carrying out the methods such as devices for delivering the G-CSF. In certain embodiments, the kit can comprise components useful for the safe disposal of devices for delivering the G-CSF, e.g., a sharps container for used syringes.

In one embodiment, the G-CSF in the kit is formulated for subcutaneous administration. In another embodiment, the G-CSF in the kit is formulated for intramuscular administration. In another embodiment, the G-CSF in the kit is formulated for intravascular administration.

The kit may further contain other active compounds, such as CSFs (e.g., G-CSF, GMCSF, and macrophage CSF), erythropoietin, stem cell factors, anti-inflammatory agents, interleukins, etc.

In one embodiment, the G-CSF in the kit is contained in an implantable device for slow release after implantation of the device. In another embodiment, the G-CSF in the kit is contained in a transdermal patch for slow release after application of the transdermal device.

In another embodiment, the present invention provides a transdermal patch comprising G-CSF as an active ingredient. In another embodiment, the present invention provides an implantable device comprising G-CSF as an active ingredient. In yet another embodiment, the present invention provides an implantable device G-CSF embedded in an inert matrix.

In another embodiment, the present invention provides a vaginal ring comprising G-CSF as an active ingredient and in some cases with another complimentary agent as an additional active ingredient.

The present invention is further illustrated by the following examples which should not be construed as limiting. The contents of all references, patents and published patent applications cited throughout this application, as well as the Figures and Tables are incorporated herein by reference.

Example 1

G-CSF Prevents Embryotoxic Effects of Cells from Women with Recurrent Spontaneous Abortion In Vitro G-CSF is effective in preventing the death of mouse embryos in an in vitro clinical assay for spontaneous abortion. Mouse bioassays have widely been used to detect embryotoxic effects of sera from subjects having reproductive difficulty. (See, Cameo, et al., 1999, Human Reprod. 14(4):959-63, Oksenberg and Brautbar 1986, Am. J. Reprod Immunol. Microbiol 11(4):118-24, Roussev et al., 1995, Am. Reprod. Immunol. 33(2):171-175 and Thomason et al., 1995, Am. J. Reprod. Immunol. 34(6):338-41).

In the in vitro clinical assay, mononuclear leukocytes are isolated from women suffering from recurrent spontaneous abortion. The leukocytes are cultured, and the culture medium is removed from the leukocytes. This culture medium is then contacted with murine embryos. Toxic factors in the culture medium typically kill the murine embryos in this assay.

The mononuclear leukocytes are incubated with G-CSF prior to removal of the culture medium. The culture medium is then removed from the leukocytes and contacted with murine embryos. Survival of the murine embryos indicates the reduction of embryotoxic factors in the culture medium and thereby the effectiveness of G-CSF administration for prevention of spontaneous abortion in this in vitro model.

Example 2

G-CSF Prevents Spontaneous Abortion in a Mouse Model In Vitro

G-CSF effectively inhibits a well-known in vivo model for spontaneous abortion.

The murine mating pair CBA×DBA/2 (see e.g., Yabuki et al., 2003, Exp. Anim. 52(2)159-63) results in a spontaneous abortion rate of approximately 40%. In this example, female CBA mice are treated according to the methods of the invention. They are treated with G-CSF prior to mating, at the time of mating and immediately after mating. A reduction of the rate of spontaneous abortion in mice treated with G-CSF relative to control mice indicates that G-CSF effectively prevents spontaneous abortion in this in vivo model.

Example 3

G-CSF Prevents Habitual Abortion In Vivo

Thirty-one women with habitual abortion, having more than three abortions, were recruited in the study (Scarpellini & Sbracia, 2004, Am. J. Repro. Imm. 51(6)433-4). The cytogenetic studies, hysterosalpingography, ultrasound, endometrial biopsy, hormonal assays (estradiol, progesterone, prolactin, thyroid hormones, etc.) diabetes workup and autoantibody tests (ACA, AND, AMA, SMA and anti-lupus Ab) were unremarkable. All of the women failed a previous treatment with Igs, or corticosteroid and aspirin in the former pregnancy. Sixteen women were randomly chosen and treated with filgrastim at 100 mg/day SC, which was started the sixth day after ovulation and continued through the 35th day after ovulation. The other fifteen women received a placebo and progesterone.

In the group receiving filgrastim, 14 of 16 became pregnant and maintained pregnancy during the recording period. The karyotype of the fetuses was normal. In the control group, only four pregnancies occurred. hCG levels in the treated women were increased by a third over the levels observed in the control women.

Over the course of the last 4 years, three patients undergoing assisted reproduction procedures have been treated with recombinant hG-CSF (rhG-CSF). Case studies of these three patients are provided below.

(1) J.C.

J.C. is a 36-year-old married white female with an obstetrical history of three uncomplicated vaginal deliveries at full term (all male children) followed by six consecutive first trimester miscarriages (each at 10-12 weeks). Conception was natural in each of the successful pregnancies and in each miscarriage. Each miscarried fetus was karyotyped, and all were normal. The couple then experienced three years of secondary infertility. At that point, she sought a consultation with a reproductive endocrinologist (RE).

The RE performed a detailed workup to attempt to identify the cause of the couple's reproductive failures. No anatomic or endocrinologic etiology was identified. Both J.C. and her husband were found to be karyotypically normal. A standard andrology workup for the husband was negative.

J.C.'s past medical history was significant in that J.C. had a remote past history of seasonal allergies and ten years of allergy desensitization shots. Based on this medical history, a series of immunologic tests including measurement of Th1 and Th2 cytokine production in vitro were ordered. As noted previously in this application, allergy is a classic Th2 immunopathologic response. Although few allergists realize it, allergy desensitization works by presenting the allergen in a manner that favors Th1 cytokine production instead of Th2 cytokine production. In many individuals, this shift from Th2 to Th1 dominance becomes more generalized and antigen non-specific. The series of tests ordered for J.C. specifically measured Th1/Th2 cytokines produced by the patient's peripheral blood mononuclear cells (PBMC) in response to the non-specific mitogen phytohemagglutinin (PHA). J.C.'s PBMC produced greater than 10,000 units per ml of the prototypic Th1 cytokine gamma interferon in response to PHA. Levels of the prototypic Th2 cytokine IL-4 and the counter regulatory Th2 cytokine IL-10 were undetectable.

The RE performed intrauterine insemination (IUI) using J.C.'s husband's sperm. The first attempt at IUI resulted in a positive HCG at 7 days. The rhG-CSF administration was initiated the following day. The regimen consisted of 100 mcg/day of rhG-CSF (Neupogen) injected subcutaneously for a total of 30 days, a cumulative dose of 3000 mcg. The rhG-CSF regimen was carried out for the full 30 days and then discontinued. The patient experienced no rhG-CSF-related side effects at any point during the regimen.

At day 14 of the rhG-CSF regimen, another blood sample was obtained from J.C. for repeat measurement of Th1 and Th2 cytokines by her PBMC in response to PHA. The repeat results showed undetectable levels of the prototypic Th1 cytokine gamma interferon and elevated levels (2,000 units per ml) of the counter regulatory $Th_2$ cytokine IL-10. These results clearly indicated that rhG-CSF produced a shift from Th1 to Th2 cytokine production by her PBMC in response to PHA. Interestingly, J.C.'s allergies had also returned. This is consistent with the shift from Th1 to Th2 cytokine dominance.

At 8 weeks, an ultrasound confirmed an ongoing healthy pregnancy with a well-formed gestational sac and a fetus with a strong heartbeat. The pregnancy continued to progress uneventfully and at 11 weeks J.C. was transferred from the care of her RE to the care of a general obstetrician. The pregnancy progressed without complication, and a healthy 8 lb., 19-inch female was delivered by planned cesarean section at 38 weeks. Mother and child are both doing well.

(2) N.C.

N.C. is a healthy 35-year-old married white female with an obstetrical history of primary infertility including three failed IUIs and one failed IVF.

N.C.'s first IUI resulted in monozygotic twins, one of which revealed no fetal heartbeat at 6 weeks and the other which had a confirmed weak fetal heartbeat at 6 weeks but no heartbeat by the $7^{th}$ week. The second WI resulted in a singleton pregnancy and fetal demise at 8 weeks. A heartbeat was seen at the $7^{th}$ week but was negative by the $8^{th}$ week. Karyotyping was performed and revealed an abnormal karyotype (69 XXY). N.C.'s third IUI resulted in a probable ectopic pregnancy treated with methotrexate. N.C.'s last pregnancy attempt was a cycle of IVF. This resulted in a confirmed and apparently healthy pregnancy at 6 weeks with a gestational sac measuring 36×37 millimeters and fetal heart rate of 113. However, one week later no fetal heartbeat was observed. The products of conception were expelled in large clots, and karyotyping was performed. Karyotyping was revealed to be normal (46 XY). N.C.'s RE performed an exhaustive workup to determine the cause of her reproductive failures. However, the workup failed to reveal any identifiable cause.

N.C.'s past medical history was non-contributory. She appeared to be a healthy female with unexplained primary infertility and repeated pregnancy loss. A review of her medical records revealed past laboratory testing showed a normal balance of Th1 and Th2 cytokines.

Because one of N.C.'s early losses involved a karyotypically abnormal embryo (69 XXY), N.C. had arranged for preimplantation genetic diagnosis for her last (failed) IVF cycle. N.C. had two cryopreserved embryos left from that cycle, and those embryos were used for the IVF cycle with rhG-CSF. N.C. received 100 mcg per day for the seven days prior to transfer and for 30 additional days after transfer, at a cumulative dose of 3700 mcg. N.C. experienced no rhG-CSF related side effects. At 6 weeks an ultrasound evaluation of N.C. revealed a healthy pregnancy with a well-formed gestational sac (40×40 mm) and a strong heart beat (145 beats per minute). At the 10th week, N.C. was transferred from her RE's care to the high-risk obstetrical unit in a hospital where she delivered a healthy baby boy. Both mother and child are doing well.

Approximately one year later, N.C. opted to undergo another IVF cycle at a different clinic without the benefit of rhG-CSF therapy. This cycle failed and was classified as a biochemical pregnancy (positive beta HCG, no evidence of gestational sac or embryo).

A few months later, N.C. contacted the inventor to request that he provide consultation regarding the use of rhG-CSF in her next IVF cycle. The inventor agreed and a clinical plan identical to her previous IVF cycle using rhG-CSF was pursued. N.C. began rhG-CSF (100 mcg per day) five days prior to embryo transfer (i.e., on the day of oocyte retrieval) in a fresh IVF cycle. The pregnancy is ongoing and her RE has transferred her to the care of a general obstetrician. At her last examination (at 20 weeks), all measurements were normal for gestational age and fetal heartbeat was strong.

(3) J.J.

J.J. is a 33-year-old married white female with a history of primary subfertility and seven failed pregnancies. Over a period of three years, J.J. suffered three first-trimester miscarriages and three chemical pregnancies. Four of the pregnancies involved the use of fertility drugs and natural conception. Two of the pregnancies occurred through NI. The last pregnancy was a failed cycle of IVF.

J.J.'s RE performed a standard workup to attempt to determine cause for J.J.'s failures. The workup failed to identify a cause. Both members of the couple were found to be karyotypically normal. J.J. and her RE decided that she should consult with a Reproductive Immunologist. Prior to J.J.'s IVF cycle, this physician performed a battery of laboratory tests and a medical evaluation and concluded that J.J. should undergo a course of Intravenous Immunoglobulin (IVIG) to correct immune problems identified through testing. Repeat laboratory tests demonstrated that IVIG failed to correct the purported immunologic problem. J.J.'s IVF cycle resulted in an ectopic pregnancy, and J.J. required emergency surgery for a unilateral salpingectomy.

J.J. and her RE sought a consultation with the inventor and decided to undergo another cycle of IVF with rhG-CSF treatment.

J.J. underwent another cycle of IVF with frozen embryos from her previous cycle. Although J.J. was scheduled to begin rhG-CSF at 100 mcg per day five days prior to embryo transfer, J.J. was not able to begin rhG-CSF until three days before embryo transfer. The rhG-CSF was continued at 100 mcg per day for 30 days after embryo transfer. The cumulative dose of rhG-CSF was 3300 mcg. J.J. completed her course of rhG-CSF and experienced no rhG-CSF related side effects.

Two embryos were transferred. The cycle resulted in a positive beta HCG (139 at 7 days post transfer; 316 at 10 days post transfer). Six weeks post transfer, an ultrasound identified a well-formed gestational sac and a heart beat of 115.

J.J. underwent another ultrasonic evaluation at 10 weeks gestation, and a strong heartbeat was identified and all measurements were exactly appropriate for dates. J.J. was transferred to the care of a general obstetrician and delivered a healthy baby girl. Both the mother and the child are healthy and doing well.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for reducing the risk of an unsuccessful pregnancy in a human female identified as having elevated Th1 cell number, elevated Th1 cell activity, elevated amount of a Th1 cell product, decreased Th2 cell number, decreased Th2 cell activity, decreased amount of a Th2 cell product, a higher ratio of Th1 cell number to Th2 cell number, or a higher ratio of Th1 cell activity to Th2 cell activity, individually as compared to prior to pregnancy or a healthy pregnancy, comprising administering to the human female having an immune system aberration a dose of a granulocyte colony stimulating factor (G-CSF) ranging from 1 to 100 mcg (micrograms)/kg/day and wherein the female is at risk of an unsuccessful pregnancy.

2. The method of claim 1 wherein G-CSF is administered at a dose ranging from 1 mcg/kg/day to 20 mcg/kg/day.

3. The method of claim 1 wherein the G-CSF is administered at a dose ranging from 1 mcg/kg/day to 10 mcg/kg/day.

4. The method of claim 1 wherein the G-CSF is filgrastim or pegfilgrastim.

5. The method of claim 1 wherein the G-CSF is administered to a human female having an elevated Th1 cell number, elevated Th1 cell activity, elevated amount of a Th1 cell product.

6. The method of claim 1 wherein the G-CSF is administered to a human female having a higher ratio of Th1 cell number to Th2 cell number, a higher ratio of Th1 cell activity to Th2 cell activity, or both.

7. The method of claim 1 wherein the G-CSF is administered until the human female recipient has a normal Th1 response, a normal Th2 response, or both.

8. The method of claim 1 wherein the Th1 cell product is interferon $\gamma$.

9. The method of claim 1 wherein the Th1 cell product is tumor necrosis factor $\beta$.

10. The method of claim 1 wherein the Th1 cell product is IL-2.

11. The method of claim 1 wherein the Th2 cell product is IL-4, IL-5, IL-6, IL-10, IL-3, or any combination thereof.

12. The method of claim 1 wherein the Th2 cell product is IL-10.

13. The method of claim 1 wherein the Th1 cell product is interferon $\gamma$, tumor necrosis factor $\beta$ or both, and the Th2 cell product is IL-10.

14. The method of claim 1 wherein the human female previously had one or more spontaneous abortions, two or more spontaneous abortions, or recurrent spontaneous abortions.

15. The method of claim 1 wherein the human female recipient is in the first trimester of pregnancy, or is in the first or second month of pregnancy.

16. The method of claim 1 wherein the G-CSF is administered daily.

17. The method of claim 1 wherein the G-CSF is administered daily for one week.

18. The method of claim 1 wherein the G-CSF is administered daily for two weeks.

19. The method of claim 1 wherein the G-CSF is administered daily for four, three, two or one week during the first trimester of pregnancy.

20. The method of claim 1 wherein the G-CSF is administered for at least five consecutive days during the first or second trimester of pregnancy, or for at least five consecutive days during the first or second week of pregnancy.

21. The method of claim 1 wherein the G-CSF is administered through the end of pregnancy.

22. The method of claim 1 wherein the G-CSF is administered for the duration of pregnancy.

23. The method of claim 1 wherein the G-CSF is administered daily for one to thirty-five consecutive days.

24. The method of claim 1 wherein the G-CSF is administered in the first 20 weeks of pregnancy.

25. The method of claim 24 wherein the G-CSF is administered for one day, two days, three days, four days, or five days.

26. The method of claim 1 wherein the G-CSF is administered in the first or second month of pregnancy.

27. The method of claim 1 wherein the G-CSF is administered daily until the end of the first trimester.

28. The method of claim 1 wherein the G-CSF is administered during the first or second trimester of pregnancy.

29. The method of claim 1 wherein the G-CSF is administered in the second trimester of pregnancy, third trimester of pregnancy, or both.

30. The method of claim 1 wherein the G-CSF is administered for four, three, two or one week.

31. The method of claim 1 wherein the G-CSF is administered for five, four, three, or two days.

32. The method of claim 1 wherein the G-CSF is administered parenterally, enterally, subcutaneously, percutaneously, transdermally, intradermally, intravenously, topically, by inhalation, or by implantation.

33. The method of claim 1 wherein the G-CSF is administered with another active agent.

34. The method of claim 33 wherein the other active agent is an immunosuppressive agent.

35. The method of claim 1 wherein the G-CSF is formulated as a composition comprising a pharmaceutically acceptable carrier or diluent.

36. The method of claim 1 wherein the G-CSF is formulated for prolonged delivery.

37. The method of claim 36 wherein the prolonged delivery results from a formulation comprising G-CSF conjugated to a water soluble polymer.

38. The method of claim 37 wherein the G-CSF conjugated to a water soluble polymer is pegfilgrastim.

39. The method of claim 36 wherein the G-CSF is formulated for prolonged delivery with a polymeric or a hydrophobic material.

40. The method of claim 36 wherein the prolonged delivery formulation comprises an inert matrix or device.

41. The method of claim 36 wherein the prolonged delivery formulation comprises an adhesive disc or patch capable of slowly releasing G-CSF for percutaneous, transdermal, or intradermal adsorption.

42. The method of claim 41 wherein the disc or patch further comprise a skin permeation enhancer.

43. The method of claim 1 wherein the human female was a recipient of an assisted reproduction procedure.

44. The method of claim 43 wherein the assisted reproduction procedure is in vitro fertilization, artificial insemination, or gamete intrafallopian tube transfer.

45. The method of claim 1 wherein the G-CSF is administered subcutaneously.

* * * * *